United States Patent
Jung

(10) Patent No.: US 10,004,315 B2
(45) Date of Patent: Jun. 26, 2018

(54) SYRINGE-TYPE COSMETIC CONTAINER

(71) Applicant: YONWOO CO., LTD., Incheon (KR)

(72) Inventor: Seo-Hui Jung, Incheon (KR)

(73) Assignee: YONWOO CO., LTD., Incheon (KR)

( * ) Notice: Subject to any disclaimer, the term of this patent is extended or adjusted under 35 U.S.C. 154(b) by 8 days.

(21) Appl. No.: 15/021,181

(22) PCT Filed: Aug. 27, 2014

(86) PCT No.: PCT/KR2014/007963
§ 371 (c)(1),
(2) Date: Mar. 10, 2016

(87) PCT Pub. No.: WO2015/037841
PCT Pub. Date: Mar. 19, 2015

(65) Prior Publication Data
US 2016/0220008 A1    Aug. 4, 2016

(30) Foreign Application Priority Data

Sep. 13, 2013    (KR) ........................ 10-2013-0110128

(51) Int. Cl.
*A45D 34/00* (2006.01)
*A45D 40/00* (2006.01)
(Continued)

(52) U.S. Cl.
CPC ............ *A45D 34/00* (2013.01); *A45D 34/04* (2013.01); *A45D 40/00* (2013.01);
(Continued)

(58) Field of Classification Search
CPC ........ A45D 34/00; A45D 34/04; A45D 40/00; A45D 2200/055; B65D 83/0033;
(Continued)

(56) References Cited

U.S. PATENT DOCUMENTS 3,128,765 A * 4/1964 Tint ........................ A61M 5/28
                                                         604/193
3,545,607 A * 12/1970 Keller ..................... A61M 5/28
                                                         206/365
(Continued)

FOREIGN PATENT DOCUMENTS

KR    20-0423625 Y1    8/2006
KR    20-0455005 Y1    8/2011
(Continued)

OTHER PUBLICATIONS

International Search Report issued in PCT/KR2014/007963 dated Oct. 23, 2014.

*Primary Examiner* — Frederick C Nicolas
(74) *Attorney, Agent, or Firm* — Marshall, Gerstein & Borun LLP

(57) ABSTRACT

A syringe-type cosmetic container in which a push bar for moving a piston is integrally formed on an upper end of an over cap so as to provide both a sealing function of closing a discharge hole by the over cap and a function as a pressing unit that moves the piston, such that manufacturing time may be shortened and manufacturing costs may be reduced by decreasing the number of components.

4 Claims, 5 Drawing Sheets

(51) Int. Cl.
 *B65D 83/00* (2006.01)
 *A45D 34/04* (2006.01)
 *A61M 5/315* (2006.01)
 *A61M 5/31* (2006.01)

(52) U.S. Cl.
 CPC .... *B65D 83/0033* (2013.01); *A45D 2200/055* (2013.01); *A61M 5/31511* (2013.01); *A61M 2005/3104* (2013.01); *A61M 2005/31506* (2013.01); *A61M 2005/31516* (2013.01)

(58) Field of Classification Search
 CPC .... A61M 5/31511; A61M 2005/31506; A61M 2005/3104; A61M 2005/31516
 See application file for complete search history.

(56) References Cited

U.S. PATENT DOCUMENTS 3,845,762 A * 11/1974 Cloyd .................... A61M 5/28
 604/193
4,213,456 A * 7/1980 Bottger ............. A61M 5/31511
 600/576
4,664,299 A * 5/1987 Goncalves ............. A45D 19/02
 222/327

FOREIGN PATENT DOCUMENTS

KR 20-0461736 Y1 8/2012
KR 20-0465396 Y1 2/2013

* cited by examiner

[Fig. 1]
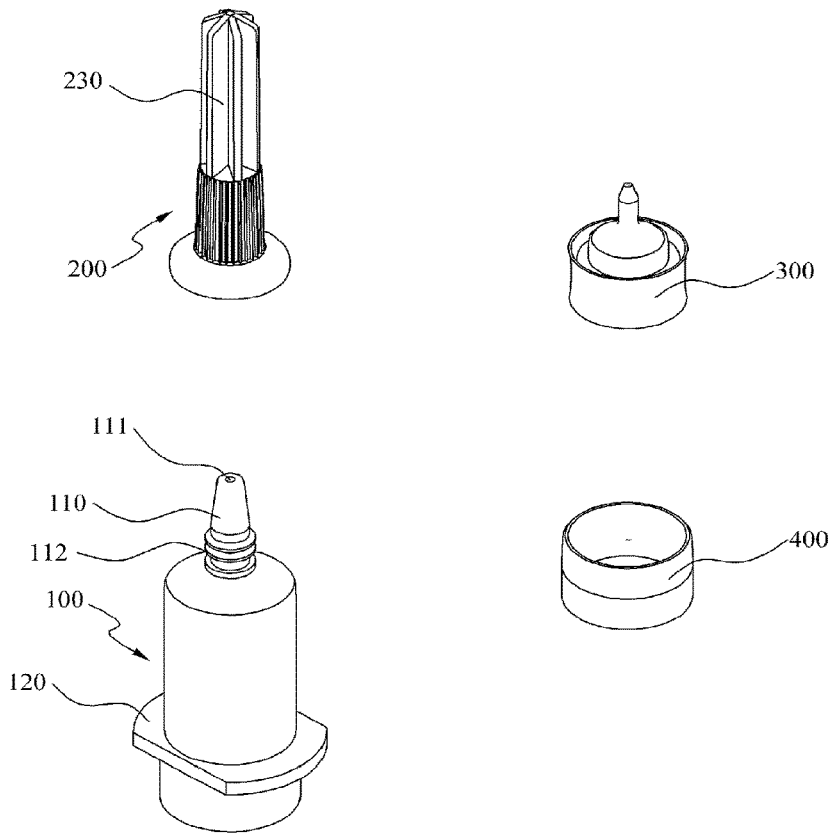
[Fig. 2]
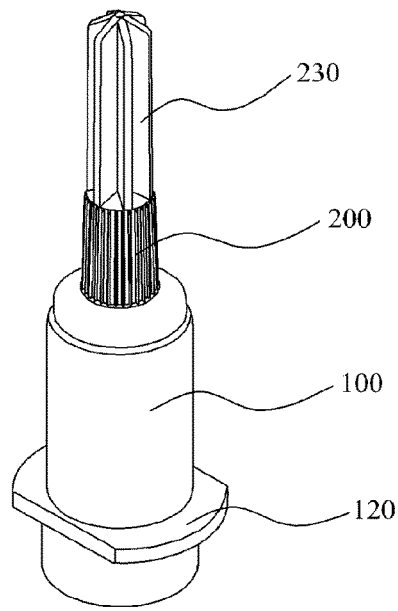

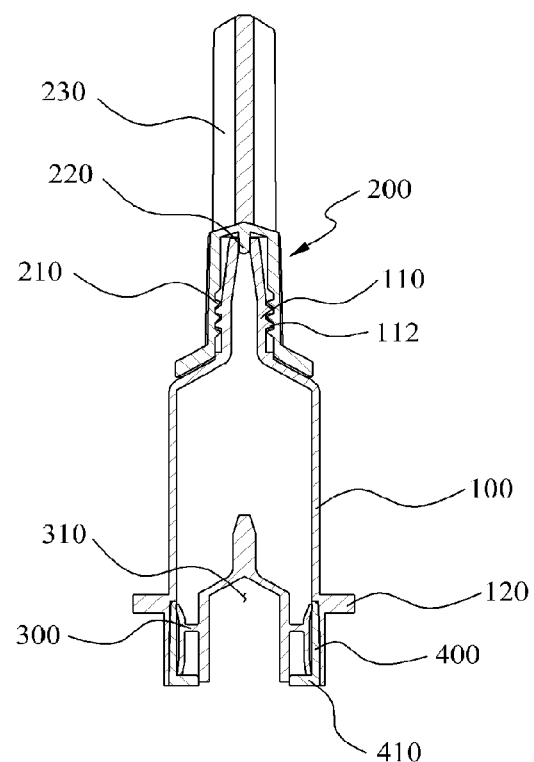
[Fig. 3]

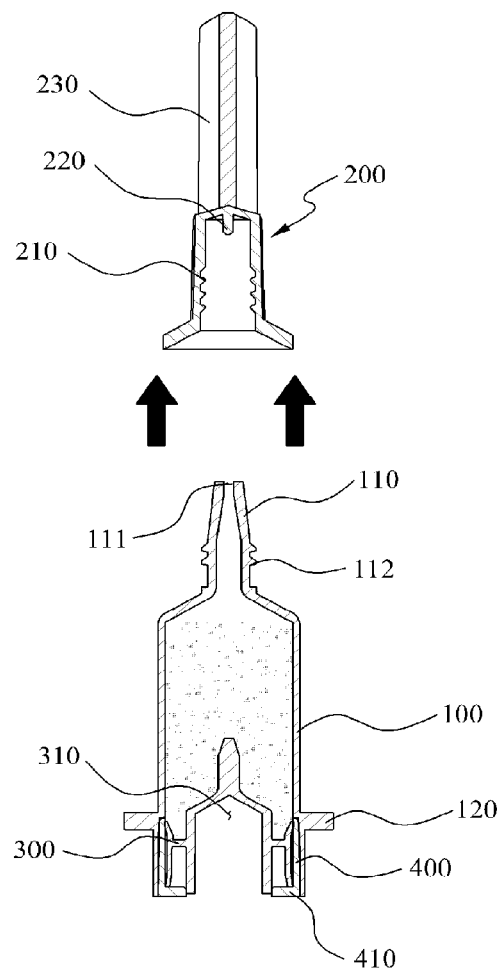
[Fig. 4]

[Fig. 5]
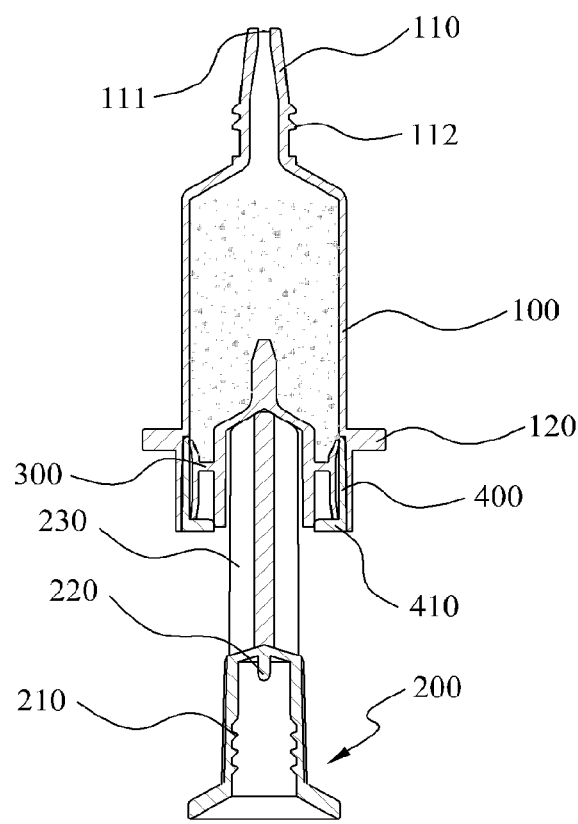

[Fig. 6]
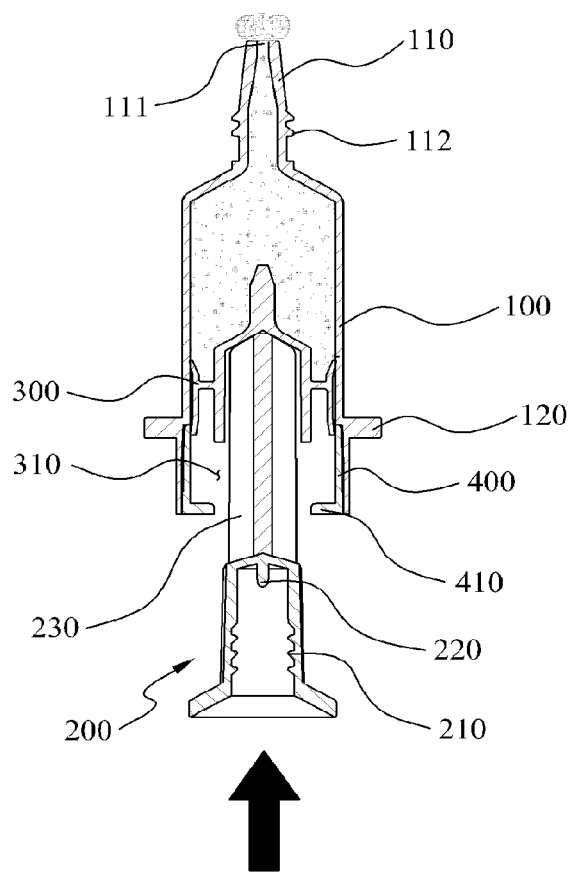

SYRINGE-TYPE COSMETIC CONTAINER

TECHNICAL FIELD

The present invention relates to a syringe-type cosmetic container, and more particularly, to a syringe-type cosmetic container, in which a push bar for moving a piston is integrally formed on an upper end of an over cap to provide both a sealing function for closing a discharge hole by means of the over cap and a function as a pressing unit for moving the piston, to thereby shorten the manufacturing time and reduce manufacturing costs by reducing the number of components.

BACKGROUND

In general, containers that contain contents such as cosmetics or medicines to supply the contents as needed are known to have various shapes. In particular, syringe-type containers, in which a piston is built in a container body to supply the contents by pressing the piston, are being provided in various shapes.

The above-described syringe-type container according to the related art is disclosed in Korean Patent Registration No. 10-1234514 (hereinafter, referred to as "registered patent").

The registered patent is an invention that was filed as an earlier application by this applicant on Sep. 13, 2012 and registered. The syringe-type container includes: a syringe body accommodating a first contents; a push bar inserted into the syringe body to move forward and backward through a user's manipulation, wherein a second contents is contained in the push bar, and a first piston that is raised through the use of the second contents is provided in a lower portion of the inside of the push bar; a push bar stopper cap coupled to surround an upper portion of the push bar, wherein a content outflow hole is defined in the push bar stopper cap so that the second contents stored in the push bar move into the syringe body, and a first check valve that is opened and closed by the forward/backward movement of the push bar is disposed at an upper portion of the content outflow hole; a discharge part coupled to surround an upper portion of the syringe body, wherein a content discharge hole through which the mixed contents of the first and second contents stored in the syringe body are discharged is defined in the discharge part, and a second check valve that is opened and closed by the forward/backward movement of the push bar is disposed at an upper portion of the content discharge hole; and an over cap detachably coupled while surrounding the discharge part to open and close a nozzle.

However, since the syringe-type container disclosed in the registered patent includes the push bar and the over cap that are separated from each other, not only may manufacturing take a long time, but the manufacturing costs may also increase due to an increase in the number of components.

The present invention has been made to solve the foregoing problems, and a goal of the prevent invention is to provide a syringe-type cosmetic container, in which a push bar for moving a piston is integrally formed on an upper end of an over cap to provide both a sealing function for closing a discharge hole by means of the over cap and a function as a pressing unit that moves the piston, to thereby shorten the manufacturing time and reduce manufacturing costs by reducing the number of components.

SUMMARY OF THE DISCLOSURE

To solve the foregoing problems, a syringe-type cosmetic container according to the present invention including: a syringe body accommodating contents therein and including a nozzle part having a discharge hole for discharging the contents on an end of one side thereof; an over cap surrounding the nozzle part and detachably screw-coupled to the syringe body; and a piston that is disposed to be slidably movable in a state in which the piston is closely attached to an inner circumferential surface of the syringe body, the syringe-type cosmetic container being characterized in that a push bar extending by a predetermined length from an upper end of the over cap is integrally formed on the over cap, and a push bar insertion groove into which the push bar is inserted is defined in the piston, wherein, after the over cap being released from being screw-coupled to the nozzle part, as the over cap is pressed in a state in which the push bar disposed on the upper end of the over cap is inserted into the push bar insertion groove, the piston is moved to discharge the contents accommodated in the syringe body through the discharge hole.

Also, a piston support including a seat protrusion that supports a lower end of the piston to prevent the piston from being separated may be coupled to an end of the other side of the syringe body.

Also, a handle part for supporting a finger of a user when the over cap is pressed may be disposed on an outer circumferential surface of the syringe body.

Also, a front end of the piston may have a shape corresponding to that of the nozzle part of the syringe body to completely use up the contents accommodated in the syringe body.

Also, a blocking rod coupled to the discharge hole defined in the nozzle part to block liquid leakage of the contents may be disposed in a central portion of the inside of the over cap.

As described above, according to the present invention, since the push bar for moving the piston is integrally formed on the upper end of the over cap, the sealing function for closing the discharge hole by means of the over cap and the function as the pressing unit that moves the piston may be provided together. Therefore, the number of components may be reduced, leading to shortening manufacturing time and reducing manufacturing costs.

BRIEF DESCRIPTION OF THE DRAWINGS

FIG. 1 is an exploded perspective view illustrating a configuration of a syringe-type cosmetic container according to a preferred embodiment of the present invention.

FIG. 2 is a coupled perspective view illustrating a configuration of a syringe-type cosmetic container according to a preferred embodiment of the present invention.

FIG. 3 is a cross-sectional view illustrating a configuration of a syringe-type cosmetic container according to a preferred embodiment of the present invention.

FIGS. 4 to 6 are explanatory views illustrating a method of using a syringe-type cosmetic container according to a preferred embodiment of the present invention.

DETAILED DESCRIPTION

Hereinafter, the present invention will be described in detail with reference to the accompanying drawings. Like reference numerals refer to like elements throughout.

FIG. 1 is an exploded perspective view illustrating a configuration of a syringe-type cosmetic container according to a preferred embodiment of the present invention, FIG. 2 is a coupled perspective view illustrating a configuration of a syringe-type cosmetic container according to a preferred embodiment of the present invention, and FIG. 3 is a cross-sectional view illustrating a configuration of a syringe-type cosmetic container according to a preferred embodiment of the present invention.

Referring to FIGS. 1 to 3, a syringe-type cosmetic container according to a preferred embodiment of the present invention includes a syringe body 100, an over cap 200, and a piston 300.

The syringe body 100 accommodates contents therein. A nozzle part 110 having a discharge hole 111 through which the contents discharged are disposed on an end of one side of the syringe body 100. A first screw thread 112 to which the over cap 200 may be screw-coupled is disposed on an outer circumferential surface of the nozzle part 110.

A handle part 120 for supporting a finger of a user when the over cap 200 is pressed to discharge the contents in a state in which a push bar 230 of the over cap 200 is inserted into a push bar insertion groove 310 of the piston 300 may be disposed on an outer circumferential surface of the syringe body 100.

The over cap 200 surrounds the nozzle part 110 and is detachably screw-coupled to the syringe body 100. A second screw thread 210 is disposed on an inner circumferential surface of the over cap 200, which contacts the first screw thread 112, so that the second screw thread 210 of the over cap 200 is screw-coupled to the first screw thread 112 disposed on the outer circumferential surface of the nozzle part 110.

Also, a blocking rod 220 coupled to the discharge hole 111 defined in the nozzle part 110 to block liquid leakage of the contents is disposed on a central portion of the inside of the over cap 200.

The present invention has a feature in which the push bar 230 extending by a predetermined length from the upper end of the over cap 200 is integrally formed on the over cap 200. The push bar 230 may be inserted into the push bar insertion groove 310 of the piston 300 to enable discharging of the contents by moving the piston 300 when the user presses the over cap 200.

Since the blocking rod 220 is disposed inside the over cap 200, and the push bar 230 integrally extends from an upper end of the blocking rod 220, the over cap 200 may provide both its original function for blocking the liquid leakage of the contents by means of the blocking rod 220 and the function as the pressing unit that moves the piston 300 to discharge the contents.

The piston 300 may be slidably movable in a state in which the piston 300 is closely attached to an inner circumferential surface of the syringe body 100. The present invention has a feature in which the push bar insertion groove 310 is defined in the piston 300 so that the push bar 230 is insertable. The push bar insertion groove 310 may have various shapes according to the shape of the push bar 230.

The front end of the piston 300 may have a shape corresponding to that of the nozzle part 110 of the syringe body 100 so that the contents accommodated in the syringe body 100 are completely exhaustible.

A piston support 400 for preventing the piston 300 from being separated is coupled to an end of the other side of the syringe body 100. The piston support 400 may have a hollow so that the push bar 230 is insertable and withdrawable. A seat protrusion 410 for supporting a lower end of the piston 300 is disposed on an end of the piston support 400.

Hereinafter, a method of using the syringe-type cosmetic container according to a preferred embodiment of the present invention will be described with reference to FIGS. 4 to 6. FIGS. 4 to 6 are explanatory views illustrating a method of using a syringe-type cosmetic container according to a preferred embodiment of the present invention.

Referring to FIGS. 4 to 6, in the syringe-type cosmetic container of FIGS. 4 to 6 according to a preferred embodiment, when the screw-coupled state is released to separate the over cap 200 from the nozzle part 110 in the state in which the over cap 200 is initially screw-coupled to the nozzle part 110, the discharge hole 111 that is closed by the blocking rod 220 of the over cap 200 may be opened. As described above, when the push bar 230 of the over cap 200 is inserted into the push bar insertion groove 310 of the piston 300 in the state in which the discharge hole 111 is opened, and then, the over cap 200 is pressed, the pressure may be transmitted to the piston 300 to move the piston 300. Thus, the contents accommodated in the syringe body 100 may be pushed in an extruding manner and discharged through the discharge hole 111.

That is, according to the present invention, since the push bar 230 is integrally formed on the upper end of the over cap 200, ordinarily, the discharge hole 111 may be closed by the blocking rod 220 of the over cap 200 to block liquid leakage of the contents. When the contents are discharged, the push bar 230 integrally formed with the over cap 200 may be coupled to the push bar insertion groove 310 and thus used as the pressing unit.

Hitherto, the best mode was disclosed in the drawings and specification. While specific terms were used, they were not used to limit the meaning or the scope of the present invention described in claims, but merely used to explain the present invention. Accordingly, a person having ordinary skill in the art will understand from the above that various modifications and other equivalent embodiments are also possible. Hence, the real protective scope of the present invention shall be determined by the technical scope of the accompanying claims.

The invention claimed is:
1. A syringe-type cosmetic container comprising:
a syringe body accommodating contents therein and comprising a nozzle part having a discharge hole for discharging the contents on an end of one side thereof; an over cap surrounding the nozzle part and detachably screw-coupled to the syringe body; and a piston disposed to be slidably movable in a state in which the piston is closely attached to an inner circumferential surface of the syringe body, the syringe-type cosmetic container being characterized in that a push bar extending by a predetermined length from an upper end of the over cap is integrally formed on the over cap, and a push bar insertion groove into which the push bar is inserted is defined in the piston,
wherein, after the over cap being released from being screw-coupled to the nozzle part, as the over cap is pressed in a state in which the push bar disposed on the upper end of the over cap is inserted into the push bar insertion groove, the piston is moved to discharge the contents accommodated in the syringe body through the discharge hole;
wherein a piston support body is coupled at an end of another side of the syringe body, wherein the piston support body is provided with a seat protrusion for supporting a lower end of the piston and thereby guiding the piston to be inserted or preventing the piston from being separated, and the piston support body has an inner wall that closely contacts a side surface of the piston, and wherein a coupling groove in which the piston support is coupled is formed at an inner wall of the another side of the syringe body.

2. The syringe-type cosmetic container of claim 1, wherein a handle part for supporting a finger of a user when the over cap is pressed is disposed on an outer circumferential surface of the syringe body.

3. The syringe-type cosmetic container of claim 1, wherein a front end of the piston has a shape corresponding to that of the nozzle part of the syringe body to completely use up the contents accommodated in the syringe body.

4. The syringe-type cosmetic container of claim 1, wherein a blocking rod coupled to the discharge hole defined in the nozzle part to block liquid leakage of the contents is disposed in a central portion of inside of the over cap.

* * * * *